(12) United States Patent
Misener et al.

(10) Patent No.: US 12,207,967 B2
(45) Date of Patent: Jan. 28, 2025

(54) ULTRASOUND IMAGING SYSTEM

(71) Applicant: Bard Access Systems, Inc., Salt Lake City, UT (US)

(72) Inventors: Anthony K. Misener, Bountiful, UT (US); William Robert McLaughlin, Bountiful, UT (US); Steffan Sowards, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/725,370

(22) Filed: Apr. 20, 2022

(65) Prior Publication Data
US 2023/0338003 A1    Oct. 26, 2023

(51) Int. Cl.
*A61B 17/34*   (2006.01)
*A61B 8/00*    (2006.01)
*A61B 8/08*    (2006.01)
*A61M 25/01*   (2006.01)

(52) U.S. Cl.
CPC .......... *A61B 8/0841* (2013.01); *A61B 8/0891* (2013.01); *A61B 8/463* (2013.01); *A61B 8/465* (2013.01); *A61B 17/3403* (2013.01); *A61B 2017/3413* (2013.01); *A61M 25/0127* (2013.01)

(58) Field of Classification Search
CPC ..... A61B 8/0841; A61B 8/0891; A61B 8/463; A61B 8/465; A61B 17/3403; A61B 2017/3413; A61M 25/0127
See application file for complete search history.

(56) References Cited

U.S. PATENT DOCUMENTS

| | | | |
|---|---|---|---|
| 5,325,293 A | 6/1994 | Dorne | |
| 5,549,554 A | 8/1996 | Miraki | |
| 5,573,529 A | 11/1996 | Haak et al. | |
| 5,908,387 A | 6/1999 | LeFree et al. | |
| 5,970,119 A | 10/1999 | Hofmann | |

(Continued)

FOREIGN PATENT DOCUMENTS

| | | |
|---|---|---|
| CN | 101854853 A | 10/2010 |
| CN | 105054962 A | 11/2015 |

(Continued)

OTHER PUBLICATIONS

U.S. Appl. No. 17/112,725, filed Dec. 4, 2020 Final Office Action dated Apr. 14, 2023.

(Continued)

*Primary Examiner* — Amal Aly Farag
(74) *Attorney, Agent, or Firm* — Rutan & Tucker LLP

(57) ABSTRACT

Disclosed herein is an ultrasound imaging system used to place a catheter within a target vessel. The ultrasound imaging system includes an ultrasound probe having an ultrasound array configured to capture one or more ultrasound images of the target vessel and other anatomical targets within a target area. The ultrasound array is in communication with a console configured to automatically detect the target vessel within the one or more ultrasound images and determine a catheter purchase. The ultrasound imaging system further includes one or more sensors in communication with the console, the one or more sensors configured to detect and track one or more magnetic signatures of an elongate medical device within the target area.

17 Claims, 8 Drawing Sheets

(56) References Cited

U.S. PATENT DOCUMENTS

| | | | |
|---|---|---|---|
| 5,997,497 A | 12/1999 | Nita et al. | |
| 6,012,034 A | 1/2000 | Hamparian et al. | |
| 6,074,367 A | 6/2000 | Hubbell | |
| 6,543,642 B1 | 4/2003 | Milliorn | |
| 6,554,771 B1 | 4/2003 | Buil et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,687,386 B1 | 2/2004 | Ito et al. | |
| 6,702,749 B2 | 3/2004 | Paladini et al. | |
| 6,754,608 B2 | 6/2004 | Svanerudh et al. | |
| 6,840,379 B2 | 1/2005 | Franks-Farah et al. | |
| 6,857,196 B2 | 2/2005 | Dalrymple | |
| 7,831,449 B2 | 11/2010 | Ying et al. | |
| 9,521,961 B2* | 12/2016 | Silverstein | A61B 8/463 |
| 9,756,766 B2 | 9/2017 | Best | |
| 9,949,720 B2 | 4/2018 | Southard et al. | |
| 9,950,139 B2 | 4/2018 | Blanchard et al. | |
| 10,849,689 B1 | 12/2020 | Hu et al. | |
| 11,974,813 B1 | 5/2024 | Donhowe et al. | |
| 2003/0047126 A1 | 3/2003 | Tomaschko | |
| 2003/0106825 A1 | 6/2003 | Molina et al. | |
| 2003/0120154 A1 | 6/2003 | Sauer et al. | |
| 2004/0055925 A1 | 3/2004 | Franks-Farah et al. | |
| 2005/0000975 A1 | 1/2005 | Carco et al. | |
| 2005/0165299 A1 | 7/2005 | Kressy et al. | |
| 2006/0004290 A1 | 1/2006 | Smith et al. | |
| 2006/0015039 A1 | 1/2006 | Cassidy et al. | |
| 2006/0020256 A1 | 1/2006 | Bell et al. | |
| 2007/0043341 A1 | 2/2007 | Anderson et al. | |
| 2007/0073155 A1* | 3/2007 | Park | A61B 8/0833 600/461 |
| 2007/0199848 A1 | 8/2007 | Ellswood et al. | |
| 2007/0239120 A1 | 10/2007 | Brock et al. | |
| 2007/0249911 A1 | 10/2007 | Simon | |
| 2007/0260213 A1 | 11/2007 | Williams et al. | |
| 2008/0033293 A1 | 2/2008 | Beasley et al. | |
| 2008/0033759 A1 | 2/2008 | Finlay | |
| 2008/0051657 A1 | 2/2008 | Rold | |
| 2008/0058963 A1 | 3/2008 | Garibaldi et al. | |
| 2008/0161687 A1 | 7/2008 | Suri et al. | |
| 2008/0177186 A1 | 7/2008 | Slater et al. | |
| 2008/0300491 A1 | 12/2008 | Bonde et al. | |
| 2009/0143672 A1 | 6/2009 | Harms et al. | |
| 2009/0143684 A1 | 6/2009 | Cermak et al. | |
| 2009/0156926 A1 | 6/2009 | Messerly et al. | |
| 2009/0182224 A1 | 7/2009 | Shmarak et al. | |
| 2009/0234328 A1 | 9/2009 | Cox et al. | |
| 2009/0306509 A1 | 12/2009 | Pedersen et al. | |
| 2010/0080427 A1 | 4/2010 | Yeluri et al. | |
| 2010/0211026 A2 | 8/2010 | Sheetz et al. | |
| 2010/0305442 A1 | 12/2010 | Tierney et al. | |
| 2010/0312121 A1 | 12/2010 | Guan | |
| 2011/0028847 A1 | 2/2011 | Whitmore, III et al. | |
| 2011/0071404 A1 | 3/2011 | Schmitt et al. | |
| 2011/0166451 A1 | 7/2011 | Blaivas et al. | |
| 2011/0295108 A1* | 12/2011 | Cox | A61B 8/4444 600/424 |
| 2011/0313293 A1 | 12/2011 | Lindekugel et al. | |
| 2012/0078103 A1 | 3/2012 | Tashiro et al. | |
| 2012/0143029 A1 | 6/2012 | Silverstein et al. | |
| 2012/0165679 A1 | 6/2012 | Orome et al. | |
| 2012/0197132 A1 | 8/2012 | O'Connor | |
| 2012/0253200 A1 | 10/2012 | Stolka et al. | |
| 2013/0006102 A1 | 1/2013 | Wilkes et al. | |
| 2013/0102889 A1 | 4/2013 | Southard et al. | |
| 2013/0131499 A1 | 5/2013 | Chan et al. | |
| 2013/0218024 A1 | 8/2013 | Boctor et al. | |
| 2013/0261553 A1 | 10/2013 | Sheldon et al. | |
| 2014/0155744 A1 | 6/2014 | Pameijer | |
| 2014/0275997 A1 | 9/2014 | Chopra et al. | |
| 2015/0148668 A1 | 5/2015 | Stolka et al. | |
| 2015/0216442 A1 | 8/2015 | Lavy et al. | |
| 2015/0250437 A1 | 9/2015 | Zaiki | |
| 2015/0272553 A1 | 10/2015 | Thattari Kandiyil et al. | |
| 2015/0320325 A1 | 11/2015 | Sheehan et al. | |
| 2015/0359991 A1 | 12/2015 | Dunbar et al. | |
| 2016/0128719 A1 | 5/2016 | Cermak | |
| 2016/0213398 A1 | 7/2016 | Liu | |
| 2016/0300120 A1 | 10/2016 | Haas et al. | |
| 2016/0302772 A1 | 10/2016 | Cummins et al. | |
| 2016/0374644 A1 | 12/2016 | Mauldin, Jr. et al. | |
| 2017/0035514 A1 | 2/2017 | Fox et al. | |
| 2017/0056062 A1 | 3/2017 | Buljubasic | |
| 2017/0079551 A1 | 3/2017 | Henkel et al. | |
| 2017/0290563 A1 | 10/2017 | Cole et al. | |
| 2018/0015256 A1 | 1/2018 | Southard et al. | |
| 2018/0061546 A1 | 3/2018 | Ma et al. | |
| 2018/0125450 A1 | 5/2018 | Blackbourne et al. | |
| 2018/0132944 A1 | 5/2018 | Yan et al. | |
| 2018/0228465 A1 | 8/2018 | Southard et al. | |
| 2018/0289929 A1 | 10/2018 | Ma et al. | |
| 2018/0310955 A1 | 11/2018 | Lindekugel et al. | |
| 2019/0026438 A1 | 1/2019 | Ma et al. | |
| 2019/0298278 A1 | 10/2019 | Nachabe et al. | |
| 2020/0090331 A1 | 3/2020 | Mansi et al. | |
| 2020/0113540 A1 | 4/2020 | Gijsbers et al. | |
| 2020/0230391 A1 | 7/2020 | Burkholz et al. | |
| 2020/0234812 A1 | 7/2020 | Willybiro et al. | |
| 2020/0237403 A1* | 7/2020 | Southard | A61B 8/461 |
| 2020/0245969 A1* | 8/2020 | Tung | A61B 8/5207 |
| 2020/0315592 A1 | 10/2020 | Soleimani et al. | |
| 2020/0359990 A1 | 11/2020 | Poland et al. | |
| 2021/0015448 A1* | 1/2021 | Sokulin | G01S 7/52073 |
| 2021/0045717 A1 | 2/2021 | Schwab | |
| 2021/0059636 A1 | 3/2021 | Durfee et al. | |
| 2021/0085282 A1 | 3/2021 | Prince | |
| 2021/0138130 A1 | 5/2021 | Kotanko et al. | |
| 2021/0169585 A1 | 6/2021 | Prince et al. | |
| 2021/0186456 A1 | 6/2021 | Prince | |
| 2021/0201080 A1 | 7/2021 | Kitahara | |
| 2021/0275256 A1 | 9/2021 | Sowards et al. | |
| 2022/0022969 A1 | 1/2022 | Misener | |
| 2022/0039685 A1 | 2/2022 | Misener et al. | |
| 2022/0096797 A1 | 3/2022 | Prince | |
| 2022/0101980 A1 | 3/2022 | Rothenberg et al. | |
| 2022/0104886 A1 | 4/2022 | Blanchard et al. | |
| 2022/0117582 A1 | 4/2022 | McLaughlin et al. | |
| 2022/0142608 A1 | 5/2022 | Matsumoto | |
| 2022/0160434 A1 | 5/2022 | Messerly et al. | |
| 2022/0189610 A1 | 6/2022 | Long et al. | |
| 2022/0241014 A1 | 8/2022 | Kleyman et al. | |
| 2022/0280246 A1 | 9/2022 | Messerly et al. | |
| 2022/0304652 A1 | 9/2022 | Peterson et al. | |
| 2022/0401157 A1 | 12/2022 | Sowards et al. | |
| 2022/0406460 A1 | 12/2022 | Golan et al. | |
| 2023/0030941 A1 | 2/2023 | Han | |
| 2023/0121370 A1 | 4/2023 | Sowards et al. | |
| 2023/0147164 A1 | 5/2023 | Sowards et al. | |
| 2023/0148993 A1 | 5/2023 | Sowards et al. | |
| 2023/0225702 A1 | 7/2023 | Sakalauskas | |
| 2023/0329748 A1 | 10/2023 | Sowards et al. | |
| 2023/0380906 A1 | 11/2023 | Misener et al. | |
| 2023/0404683 A1 | 12/2023 | Schmidt et al. | |
| 2023/0420105 A1 | 12/2023 | Misener et al. | |
| 2024/0008894 A1 | 1/2024 | Sowards et al. | |
| 2024/0245386 A1 | 7/2024 | Prince | |

FOREIGN PATENT DOCUMENTS

| | | |
|---|---|---|
| CN | 216167530 U | 4/2022 |
| EP | 1504713 A1 | 2/2005 |
| EP | 0788329 B1 | 12/2006 |
| JP | 2018175547 A | 11/2018 |
| KR | 20180070878 A | 6/2018 |
| WO | 2013059714 A1 | 4/2013 |
| WO | 2015/017270 A1 | 2/2015 |
| WO | 2018/026878 A1 | 2/2018 |
| WO | 2019/232451 A1 | 12/2019 |
| WO | 2020/002620 A1 | 1/2020 |
| WO | 2020150501 A1 | 7/2020 |
| WO | 2020/186198 A1 | 9/2020 |
| WO | 2021113733 A1 | 6/2021 |

(56) References Cited

FOREIGN PATENT DOCUMENTS

| | | |
|---|---|---|
| WO | 2022/067101 A1 | 3/2022 |
| WO | 2022/072727 A2 | 4/2022 |
| WO | 2022/081904 A1 | 4/2022 |
| WO | 2022/150411 A1 | 7/2022 |
| WO | 2022/187701 A1 | 9/2022 |
| WO | 2022212414 A1 | 10/2022 |
| WO | 2022/271728 A1 | 12/2022 |
| WO | 2023064492 A1 | 4/2023 |
| WO | 2023081414 A1 | 5/2023 |
| WO | 2023091427 A1 | 5/2023 |
| WO | 2023/205019 A1 | 10/2023 |
| WO | 2023/205052 A1 | 10/2023 |
| WO | 2023/230284 A1 | 11/2023 |
| WO | 2023/244640 A1 | 12/2023 |
| WO | 2023/250001 A1 | 12/2023 |
| WO | 2024/010874 A1 | 1/2024 |

OTHER PUBLICATIONS

U.S. Appl. No. 17/485,035, filed Sep. 24, 2021 Non-Final Office Action dated May 3, 2023.
PCT/US2022/022400 filed Mar. 29, 2022 International Search Report and Written Opinion dated Jul. 8, 2022.
PCT/US2022/034380 filed Jun. 21, 2022 International Search Report and Written Opinion dated Oct. 5, 2022.
Murphy, Ethan K., et al., "Phantom Studies of Fused-Data TREIT Using Only Biopsy-Probe Electrodes" IEEE Transactions on Medical Imaging, IEEE, USA. vol. 39 No. 114, May 2020. (May 4, 2020).
PCT/US2012/061182 International Seach Report and Written Opinion dated Mar. 11, 2013.
PCT/US2020/063441 filed Dec. 4, 2020 International Preliminary Report on Patentability dated May 17, 2022.
PCT/US2020/063441 filed Dec. 4, 2020 International Search Report and Written Opinion dated Mar. 19, 2021.
PCT/US2021/052055 filed Sep. 24, 2021 International Search Report and Written Opinion dated Dec. 20, 2021.
PCT/US2022/019017 filed Mar. 4, 2022 International Search Report and Written Opinion dated Jun. 14, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/951,903, filed Apr. 12, 2018 Advisory Action dated Dec. 22, 2020.
U.S. Appl. No. 15/951,903, filed Apr. 12, 2018 Board Decision dated Apr. 20, 2022.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 15/951,903, filed Apr. 12, 2018 Notice of Allowance dated May 2, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
Beigi, P. et al., "Enhancement of needle visualization and localization in ultrasound." International Journal of Computer Assisted Radiology and Surgery, vol. 16, No. 130, Sep. 2020 [Sep. 30, 2020] pp. 169-178.
PCT/US2023/018340 filed Apr. 12, 2023 International Seach Report and Written Opinion dated Jul. 20, 2023.
PCT/US2023/018680 filed Apr. 14, 2023 International Seach Report and Written Opinion dated Aug. 11, 2013.
PCT/US2023/023616 filed May 25, 2023 International Search Report and Written Opinion dated Aug. 16, 2023.
PCT/US2023/025259 filed Jun. 14, 2023 International Search Report and Written Opinion dated Sep. 25, 2023.
PCT/US2023/025845 filed Jun. 21, 2023 International Search Report and Written Opinion dated Sep. 26, 2023.
PCT/US2023/027042 filed Jul. 6, 2023 International Search Report and Written Opinion dated Oct. 10, 2023.
Schmidt G A et al Ultrasound-guided 1-22 vascular access in critical illness Intensive Care Medicine Springer Berlin Heidelberg Berlin/Heidelberg vol. 45 No. 4 Feb. 18, 2019 Feb. 18, 2019 pp. 434-446 XP036747615 ISSN 0342-4642 DOI 10.1007/S00134-019-05564-7 retrieved on 2019-02-181.
U.S. Appl. No. 17/485,035, filed Sep. 24, 2021 Notice of Allowance dated Nov. 8, 2023.
U.S. Appl. No. 17/707,662, filed Mar. 29, 2022 Non-Final Office Action dated Oct. 17, 2023.
U.S. Appl. No. 17/707,662, filed Mar. 29, 2022 Advisory Action dated Feb. 23, 2024.
U.S. Appl. No. 17/707,662, filed Mar. 29, 2022 Final Office Action dated Apr. 22, 2024.
U.S. Appl. No. 17/724,371, filed Apr. 19, 2022 Non-Final Office Action dated Apr. 12, 2024.
U.S. Appl. No. 17/825,976, filed May 26, 2022 Restriction Requirement dated Apr. 12, 2024.
PCT/US2022/046606 filed Oct. 13, 2022 International Search Report and Written Opinion dated Feb. 6, 2023.
PCT/US2022/049042 filed Nov. 4, 2022 International Search Report and Written Opinion dated Mar. 1, 2023.
PCT/US2022/049989 filed Nov. 15, 2022 International Search Report and Written Opinion dated Feb. 6, 2023.
U.S. Appl. No. 17/112,735, filed Dec. 4, 2022 Non-Final Office Action dated Oct. 26, 2022.
U.S. Appl. No. 17/707,662, filed Mar. 29, 2022 Final Office Action dated Dec. 20, 2023.
U.S. Appl. No. 17/724,371, filed Apr. 19, 2022 Final Office Action dated Jul. 24, 2024.
U.S. Appl. No. 17/849,455, filed Jun. 24, 2022 Non-Final Office Action dated Jul. 18, 2024.
U.S. Appl. No. 17/859,980, filed Jul. 7, 2022 Non-Final Office Action dated Jul. 1, 2024.
U.S. Appl. No. 17/724,371, filed Apr. 19, 2022 Advisory Action dated Sep. 20, 2024.
U.S. Appl. No. 17/825,976, filed May 26, 2022 Non-Final Office Action dated Oct. 4, 2024.
U.S. Appl. No. 17/981,313, filed Nov. 4, 2022 Non-Final Office Action dated Oct. 8, 2024.
U.S. Appl. No. 18/601,980, filed Mar. 11, 2024 Non-Final Office Action dated Sep. 27, 2024.

\* cited by examiner

ULTRASOUND IMAGING SYSTEM

BACKGROUND

Determining a catheter purchase (e.g., length of catheter within a target vessel) is important for selecting the correct catheter and correct trajectory to access the target vessel. Current methods of determining the catheter purchase rely on fixed points on an ultrasound image determined by a user. It would be beneficial to the clinician and the patient to have an ultrasound imaging system that automatically determines the catheter purchase using automated vessel detection and needle tracking technologies. Disclosed herein is an ultrasound imaging system and method of use that address the foregoing.

SUMMARY

Disclosed herein is an ultrasound imaging system used to place a catheter within a target vessel. The ultrasound imaging system includes: an ultrasound probe having an ultrasound array configured to capture one or more ultrasound images of the target vessel within a target area; a console in communication with the ultrasound probe; and a medical device tracking system in communication with the console, where the medical device tracking system is configured to determine a position and/or orientation of a needle within the target area. The console includes logic configured to automatically detect the target vessel within the one or more ultrasound images and determine a catheter purchase based on the position and/or orientation of the needle.

In some embodiments, the logic is configured to determine the catheter purchase based on a depth of the target vessel from a skin surface in the target area.

In some embodiments, the logic is configured to determine the depth of the target vessel.

In some embodiments, a user supplies the depth of the target vessel to the target vessel.

In some embodiments, the logic is configured to determine the catheter purchase based on an angle of insertion for the needle.

In some embodiments, the medical device tracking system includes one or more sensors coupled with the ultrasound probe, the one or more sensors configured to detect and track one or more magnetic signatures of the needle within the target area, and in some embodiments, the one or more sensors are configured to detect and track the angle of insertion of the needle.

In some embodiments, a user supplies the angle of insertion to the console.

In some embodiments, a display is in communication with the console, the logic is configured to depict the one or more captured ultrasound images and one or more icons relating to the catheter purchase on the display.

Also disclosed herein is a method of determining a catheter purchase including capturing one or more ultrasound images of a target area, the one or more ultrasound images having one or more target vessels and other anatomical targets, determining a depth of each of the one or more target vessels, determining an insertion site within the target area, determining an angle of insertion of an elongate medical device from the insertion site to access each of the one or more target vessels, and calculating the catheter purchase.

In some embodiments, capturing one or more ultrasound images of the target area includes an ultrasound probe having an ultrasound array in communication with a console capturing the one or more ultrasound images of the target area.

In some embodiments, determining a depth of each of the one or more target vessels includes logic of the console automatically determining a depth of each of the one or more target vessels from a skin surface within the target area.

In some embodiments, determining an insertion site within the target area includes a user or the logic determining a location of the insertion site within the target area.

In some embodiments, determining an angle of insertion of an elongate medical device from the insertion site to access each of the one or more target vessels includes the logic determining the angle of insertion of the elongate medical device by using one or more sensors coupled to the ultrasound probe, the one or more sensors configured to detect the location and orientation of the elongate medical device within the target area.

In some embodiments, the logic determining the angle of insertion of the elongate medical device by using one or more sensors includes the one or more sensors configured to detect one or more magnetic signatures of the elongate medical device.

In some embodiments, determining an angle of insertion of an elongate medical device from the insertion site to access each of the one or more target vessels includes the logic determining an optimal trajectory of the elongate medical device from the insertion site to each of the one or more target vessels, along the angle of insertion.

In some embodiments, determining an angle of insertion of the elongate medical device includes a user determining the angle of insertion of the elongate medical device.

In some embodiments, calculating the catheter purchase includes the logic calculating the catheter purchase based on one or more of the depth of the target vessel, the angle of insertion of the elongate medical device, the location of the insertion site, or the optimal trajectory of the elongate medical device needed to access the target vessel.

In some embodiments, calculating the catheter purchase includes identifying one or more catheters having a catheter purchase length necessary to access the one or more target vessels.

In some embodiments, identifying one or more catheters includes the logic identifying the one or more catheters having the catheter purchase length necessary to access the one or more target vessels.

In some embodiments, calculating the catheter purchase includes calculating the catheter purchase as the elongate medical device is moved through the target area, where moving the elongate medical device through the target area includes changing the angle of insertion.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
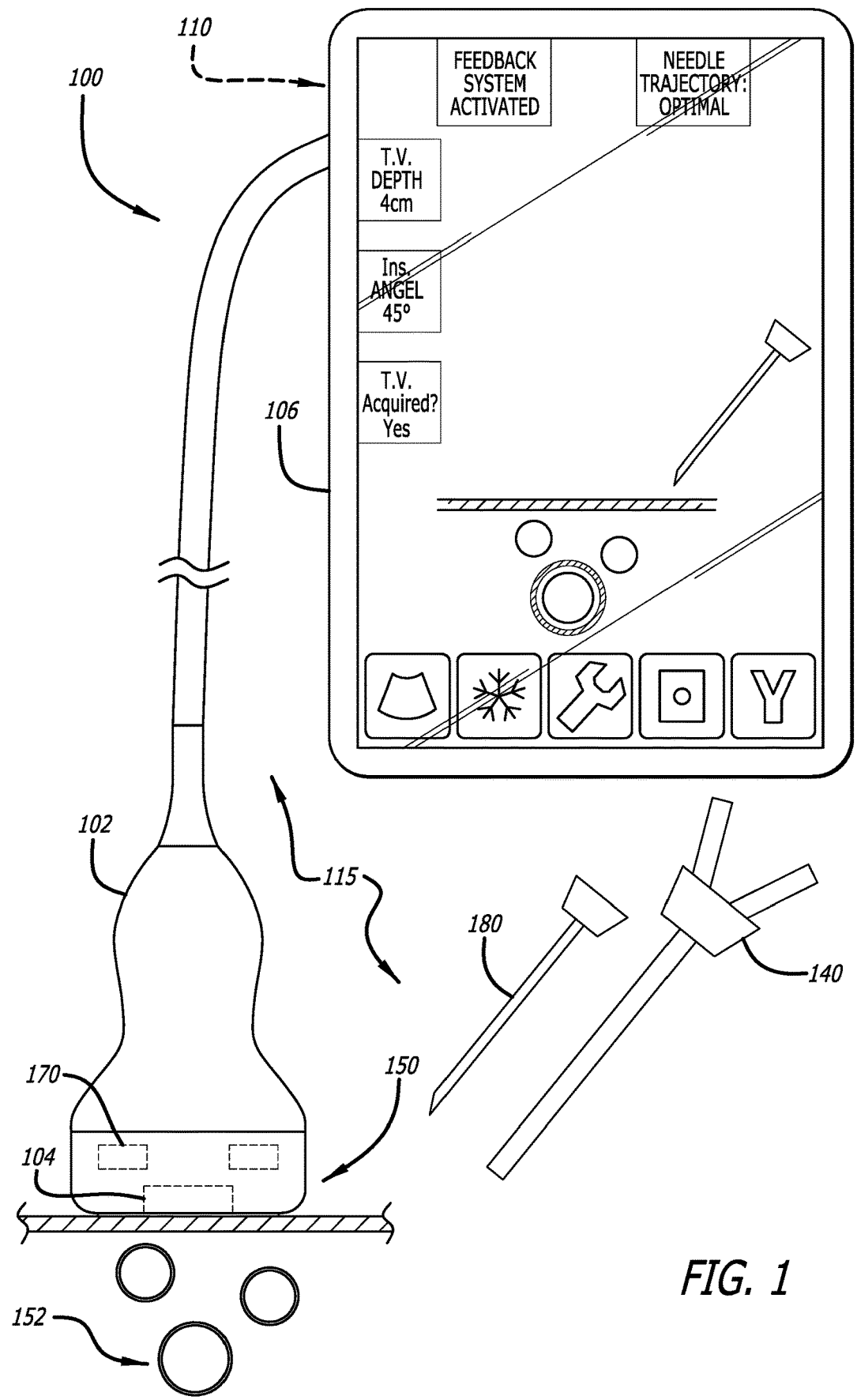
FIG. 1 illustrates a perspective view of an ultrasound imaging system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

FIG. 1 illustrates a perspective view of an ultrasound imaging system 100, in accordance with some embodiments. In some embodiments, the ultrasound imaging system 100 may be used to help place a catheter 140 within a target vessel 152. In some embodiments, the ultrasound imaging system 100 may be used calculate or otherwise determine a catheter purchase, as further described below. In some embodiments, the ultrasound imaging system 100 may include an ultrasound probe 102 having an ultrasound array 104 configured to capture one or more ultrasound images. In some embodiments, the ultrasound probe 102 including the ultrasound array 104 may be in communication with a console 110 configured to receive the one or more ultrasound images. In some embodiments, the ultrasound probe 102 may be brought into a target area 150 to capture one or more ultrasound images of one or more target vessels 152 and other anatomical targets. In some embodiments, a display 106 may be in communication with the console 110, the display 106 configured to display the one or more ultrasound images. In some embodiments, the ultrasound imaging system 100 may be configured to detect a target vessel 152, detect an angle of insertion of an elongate medical device 180, and determine catheter purchase to place the catheter 140 within the target vessel 152, as will be described in more detail herein. As used herein, an elongate medical device 180 includes a needle, guidewire, or any other medical device used to access the target vessel 152 to place the catheter 140 or any other vascular access device.

The system 100 may include or otherwise utilize a needle tracking system 115 configured to detect a position and/or orientation the needle 180 in three-dimensional space. In some embodiments, the needle tracking system 115, or portions thereof, may be included within the console 110 and/or the ultrasound probe 102. In other embodiments, the needle tracking system 115 may be separate from and coupled with the system 100. The needle tracking system 115 may incorporate various methodologies, such a visual detection (e.g., a camera with or without visual tags), or fiber optic sensing. In some embodiments, the needle tracking system 115 may incorporate mixed reality or artificial reality modalities such as those described in U.S. published application No. 2022/0031965 which is incorporated herein by reference in its entirety.

In some embodiments, the ultrasound probe 102 may include one or more sensors 170 in communication with the console 110. In some embodiments, the one or more sensors 170 may be configured to detect and track in three-dimensional space the needle 180. In some embodiments, the one or more sensors 170 may be configured to track a magnetic signature including a magnetic signature of the needle 180. In some embodiments, the one or more sensors 170 may be configured to detect and track the magnetic signature of additional devices within the target area 150 including the catheter 140, or the like.

Figure 2:
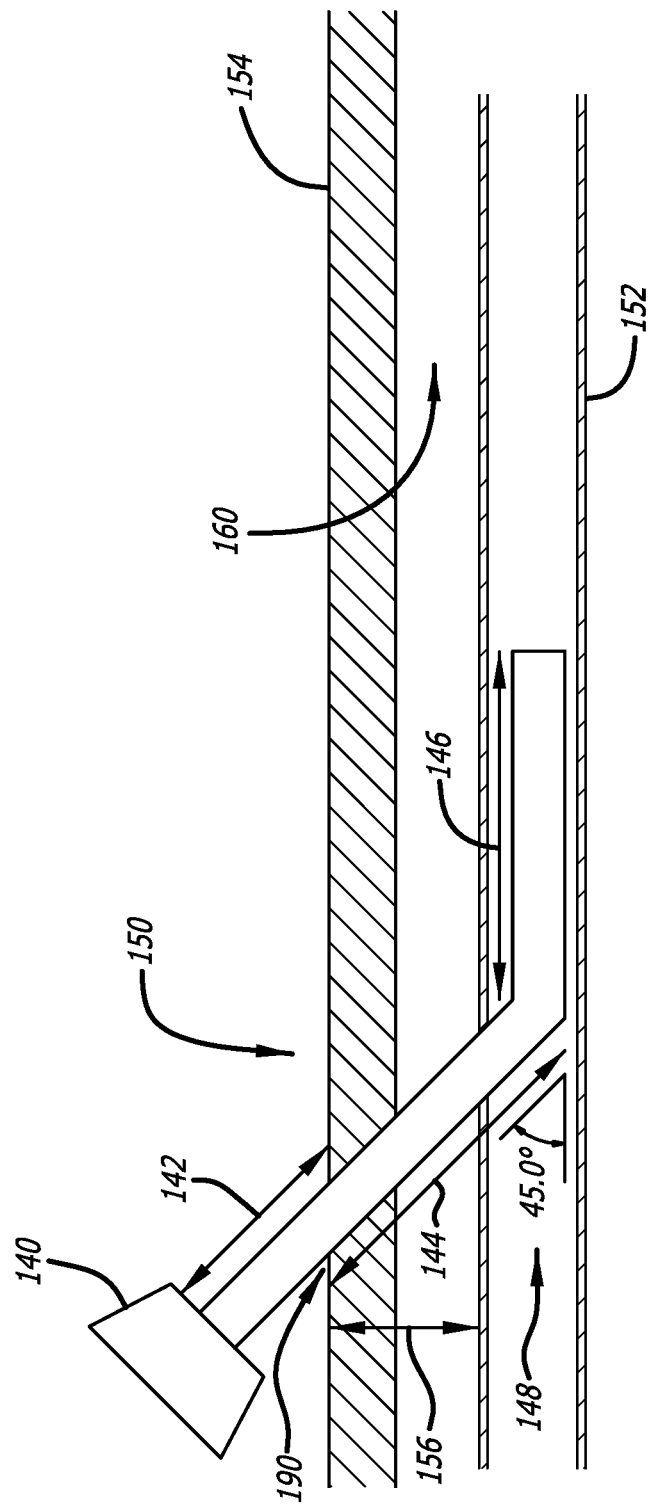
FIG. 2 illustrates a cross sectional view of a catheter placed within a target vessel, in accordance with some embodiments.

FIG. 2 illustrates a side cross sectional view of the catheter 140 placed within a target vessel 152, in accordance with some embodiments. In some embodiments, the ultrasound imaging system 100 may be used to place the catheter 140 within the target vessel 152. In properly placing the catheter 140 within the target vessel 152, "catheter purchase" must be determined. In some embodiments, catheter purchase may include (i.e., be the sum of) the length of catheter 140 within one or more tissues 160, the length of catheter 140 within the target vessel 152, and the length of catheter 140 outside of the tissues 160. In some embodiments, catheter purchase may be expressed as percentages of the catheter 140 that reside within the one or more tissues 160, within the target vessel 152, and outside of the tissues 160. In some embodiments, catheter purchase is an important factor in determining which size and length of catheter 140 to place within the target vessel 152, which vessel will be selected as the target vessel 152 taking into account vessel depth and vessel size, and appropriate trajectory of the catheter 140 needed to access the target vessel 152.

As illustrated in FIG. 2, the target vessel 152 is located at a first depth 156 from a skin surface 154. In some embodiments, the catheter 140 may have a first length 142 outside of the one or more tissues 160, a second length 144 residing within the one or more tissues 160 along a first angle 148, and a third length 146 residing within the target vessel 152. In some embodiments, the catheter 140 may be placed into the target vessel 152 at the first angle 148 relative to the target vessel 152. In some embodiments, the first angle 148 may be an angle of insertion for accessing the target vessel 152 by the needle 180 and may be used to determine catheter purchase. In some embodiments, the console 110 may be configured to determine the depth of each of the vessels 152A-152C wherein the depth may include the distance from a skin surface 154 to the center of a cross section of the vessel, may include the distance from the skin surface 154 to an outer edge of the vessel, or the like. In some embodiments, the depth may include the distance from an insertion site 190 to the target vessel 152 including along the first angle 148. In some embodiments, the needle 180 or the catheter 140 may be inserted into the target area 150 at the insertion site 190. In some embodiments, the location of the insertion site 190 within the target area 150 may be determined by the user. In some embodiments, the catheter purchase may include the sum of the first length 142, the second length 144, and the third length 146 while taking into account the first angle 148.

In some embodiments, one or more of the first length 142, the second length 144, the third length 146 or the first angle 148 may be determined by the user. By way of example, the first angle 148 may be a predefined or such as a common angle. In some embodiments, the first angle 148 may be defined by a needle guide (not shown). Similarly, the first length 142 and/or the third length 146 may be predefined the user. Further, in some embodiments, the first depth 156 may also be known or predefined by the user. As such, one or more of the first length 142, first angle 148, the first depth 156 or the third length 146 may input into the system 100 and used by the system 100 to determine/calculate the catheter purchase.

Figure 3A:
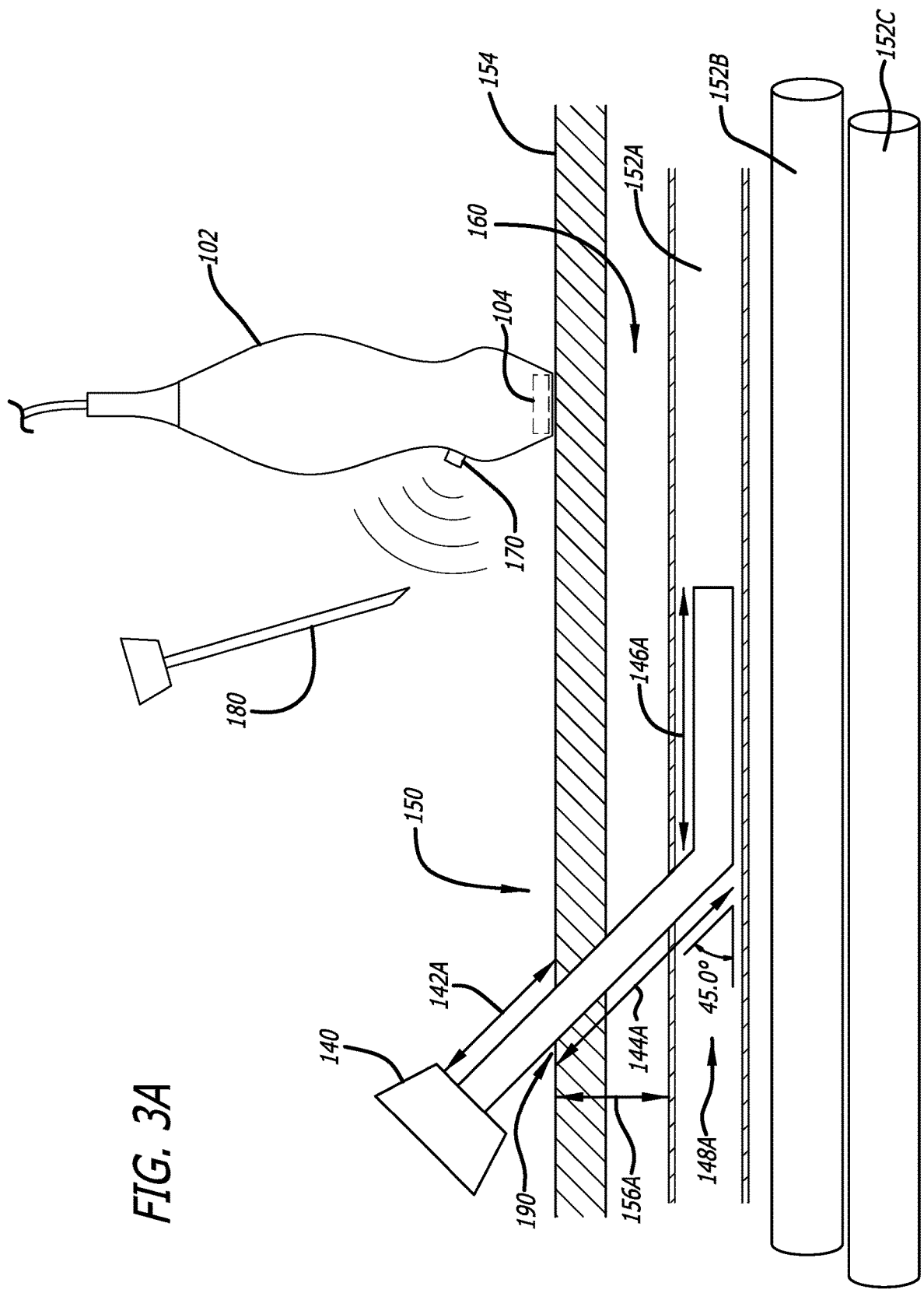
FIG. 3A illustrates a side cross sectional view of an exemplary method of capturing one or more ultrasound images of the target area having multiple target vessels therein, in accordance with some embodiments.

FIG. 3A illustrates a side cross sectional view of an exemplary method of capturing one or more ultrasound images of the target area 150 having multiple target vessels 152A-152C therein. In some embodiments, the ultrasound probe 102 may be brought into the target area 150 and the ultrasound array 104 may be configured to capture one or more ultrasound images of the target area 150 including one or more target vessels 152A-152C and other anatomical targets. In some embodiments, the target area 150 may include a first vessel 152A, a second vessel 152B, and a third vessel 152C. In some embodiments, the needle 180 may be brought into the target area 150 and tracked by the one or more sensors 170 coupled to the ultrasound probe 102. In some embodiments, each of the first vessel 152A, the second vessel 152B, and the third vessel 152C may be evaluated as potential target vessels. In some embodiments, if the first vessel 152A is selected as the target vessel, the catheter purchase may be determined for the catheter 140 to be placed into the first vessel 152A. An optimal trajectory of the needle 180 and the catheter 140 may be determined using the one or more sensors 170 tracking the needle 180 in three-dimensional space within the target area 150. The catheter 140 may have (i) the first length 142A outside of the tissues 160, (ii) the second length 144A inside the tissues 160, and (iii) the third length 146A within the first vessel 152A. In some embodiments, using the same insertion site 190, the depth of the target vessel may be configured to impact either the angle of insertion needed to access the target vessel or the catheter purchase required to place the catheter 140 within the target vessel.

Figure 3C:
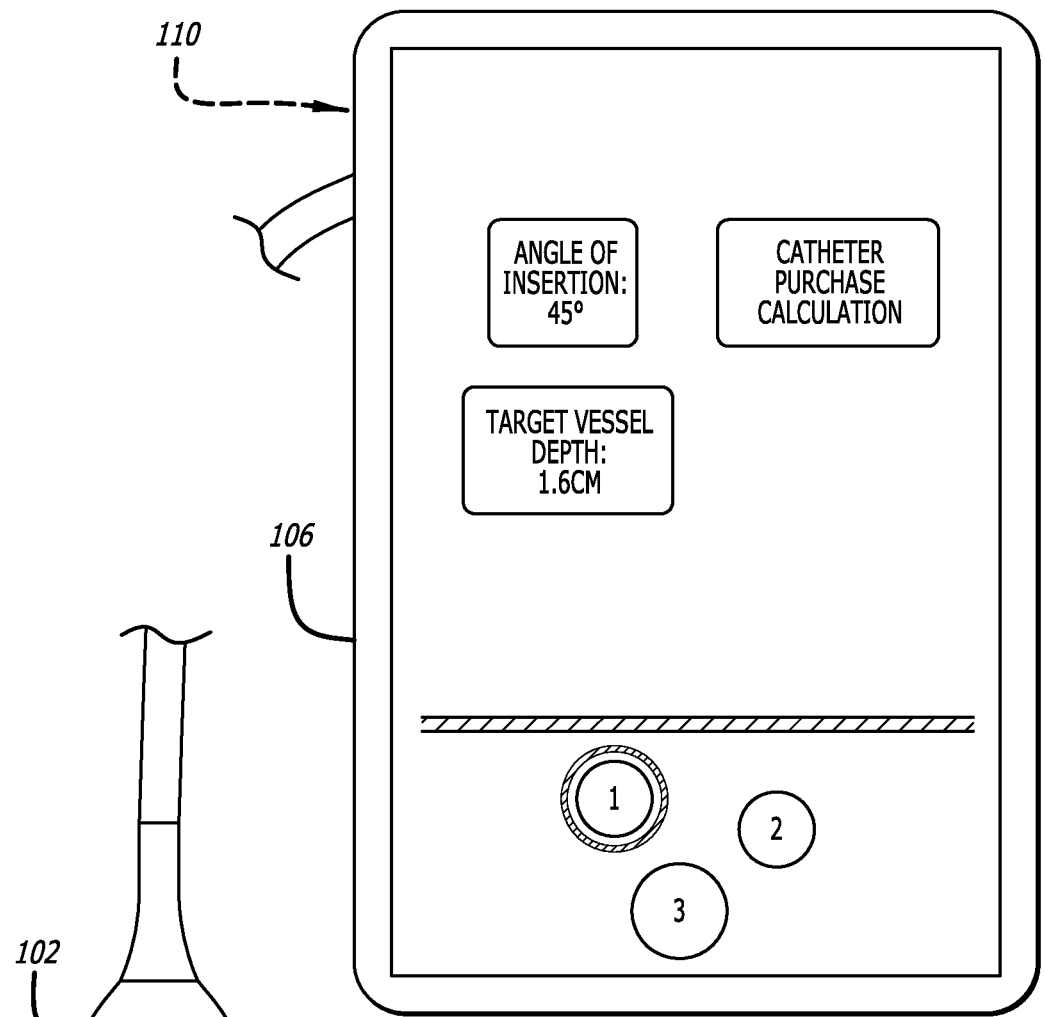
FIG. 3C illustrates a perspective view of a display depicting one of the captured ultrasound images of FIG. 3B.
Figure 3B:
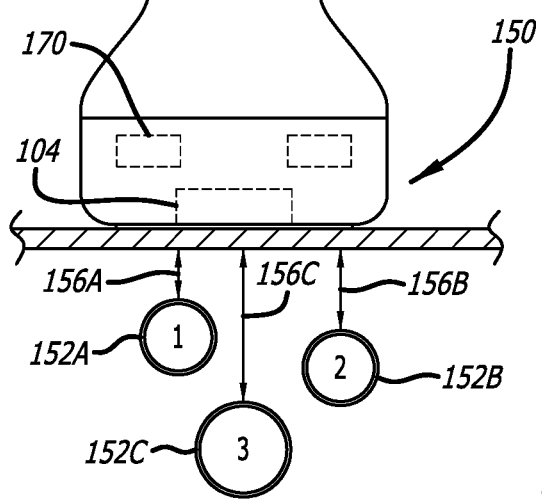
FIG. 3B illustrates a front cross sectional view of the exemplary method of capturing one or more ultrasound images of the target area of FIG. 3A, in accordance with some embodiments.

FIG. 3B illustrates a front cross sectional view of the exemplary method of capturing one or more ultrasound images of the target area 150 of FIG. 3A, in accordance with some embodiments. As illustrated in FIG. 3B, in some embodiments, the first vessel 152A may include a first vessel depth 156A, the second vessel 152B may include a second vessel depth 156B, and the third vessel 152C may include a third vessel depth 156C. In some embodiments, the second vessel depth 156B may be greater than the first vessel depth 156A and the third vessel depth 156C may be greater than the second vessel depth 156B. In some embodiments, the ultrasound array 104 may communicate the one or more captured ultrasound images to the console 110.

FIG. 3C illustrates a perspective view of the display 106 depicting one of the captured ultrasound images of FIG. 3B. The display 106 may be configured to depict one of the captured ultrasound images including the first vessel 152A, the second vessel 152B, and the third vessel 152C. In some embodiments, the console 110 may be configured to determine the depth of each of the vessels 152A-152C. In some embodiments, the display 106 may be configured to display a plurality of icons 108. In some embodiments, the plurality of icons 108 may be related to a selected target vessel, a desired target vessel depth, the actual target vessel depth, a desired angle of insertion of a medical device needed to access the target vessel, an actual angle of insertion of the medical device, a target vessel selector, a catheter purchase calculation, or the like. As illustrated in FIG. 3C, the first vessel 152A is selected on the display 106 as the target vessel and various icons 108 are depicted, demonstrating the target vessel depth (e.g., the first vessel depth 156A), the angle of insertion needed to access the first vessel 152A, and the catheter purchase calculation.

Figure 3D:
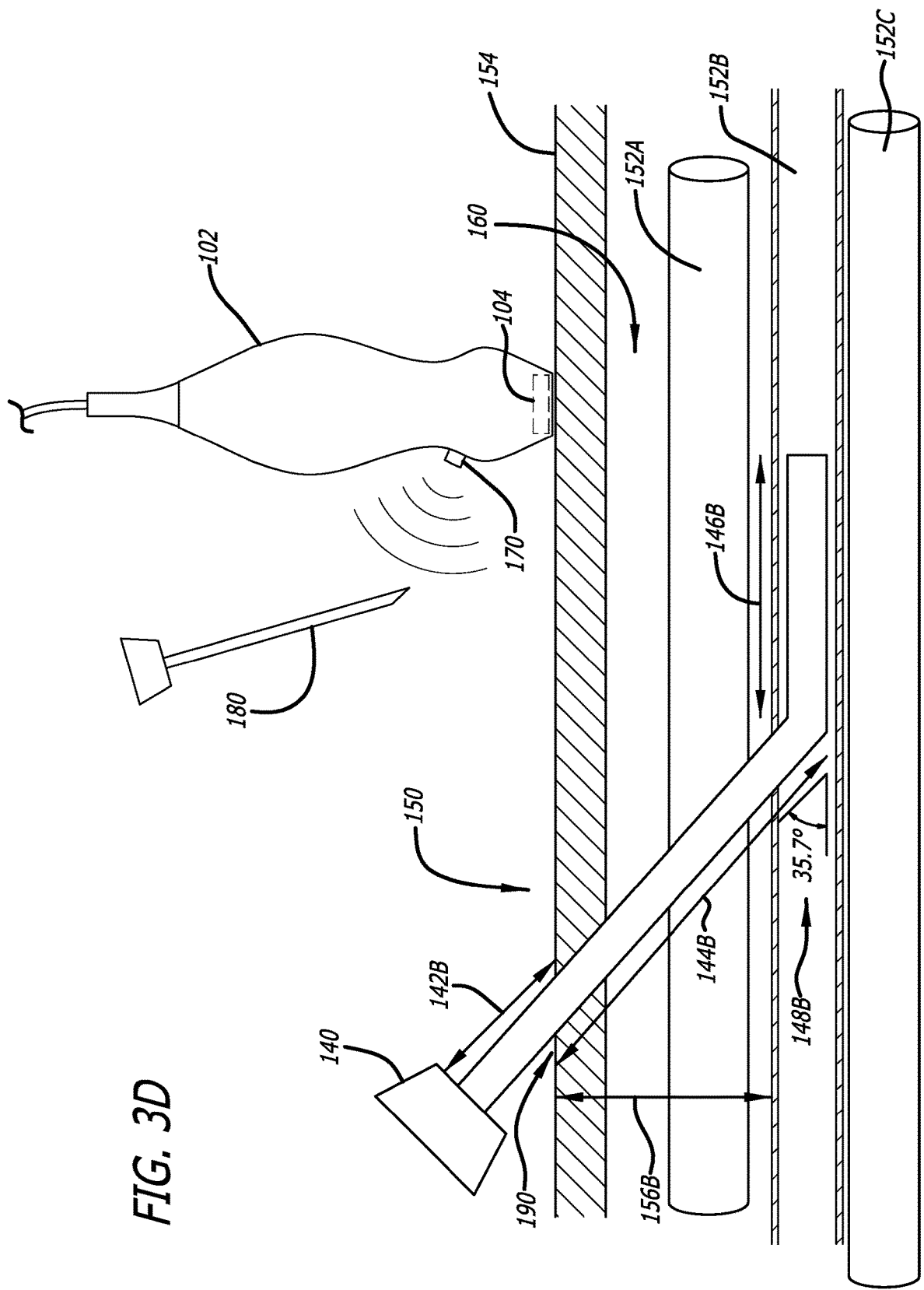
FIG. 3D illustrates a side cross sectional view of an exemplary method of capturing one or more ultrasound images of the target area having multiple target vessels therein, in accordance with some embodiments.

FIG. 3D illustrates a side cross sectional view of the exemplary method of capturing one or more ultrasound images of the target area 150 having multiple target vessels 152A-152C therein. In some embodiments, if the second vessel 152B is selected as the target vessel, the catheter purchase may be determined for the catheter 140 to be placed into the second vessel 152B. The optimal trajectory of the needle 180 and the catheter 140 may be determined using the one or more sensors 170 tracking the needle 180 in three-dimensional space within the target area 150. The catheter 140 may have the first length 142B outside of the tissues 160, the second length 144B inside the tissues 160, and the third length 146B within the second vessel 152B.

Figure 3F:
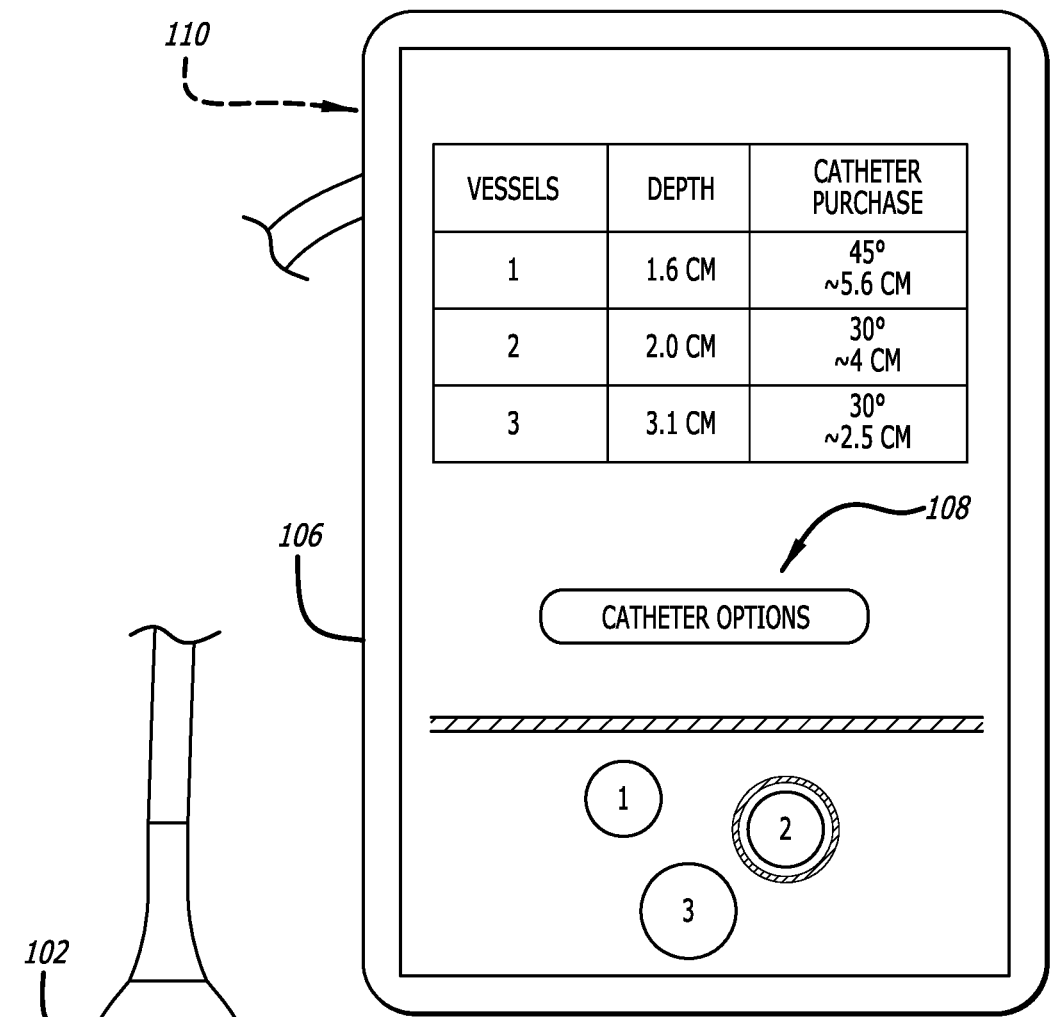
FIG. 3F illustrates a perspective view of the display depicting one of the captured ultrasound images of FIG. 3E, including a catheter purchase calculation, in accordance with some embodiments.
Figure 3E:
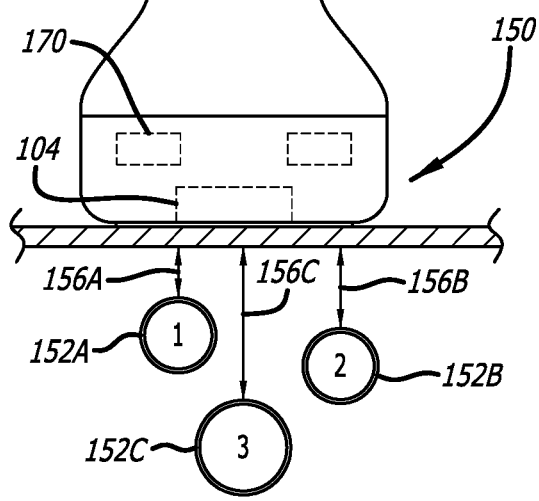
FIG. 3E illustrates a front cross sectional view of the exemplary method of capturing one or more ultrasound images of the target area of FIG. 3D, in accordance with some embodiments.

FIG. 3E illustrates a front cross sectional view of FIG. 3D. As illustrated in FIG. 3E, in some embodiments, the first vessel 152A may include a first vessel depth 156A, the second vessel 152B may include a second vessel depth 156B, and the third vessel 152C may include a third vessel depth 156C. In some embodiments, the second vessel depth 156B may be greater than the first vessel depth 156A and the third vessel depth 156C may be greater than the second vessel depth 156B. In some embodiments, the ultrasound array 104 may communicate the one or more captured ultrasound images to the console 110.

FIG. 3F illustrates a perspective view of the display 106 depicting the catheter purchase determination, in accordance with some embodiments. Once the console 110 receives the one or more ultrasound images, the console 110 may be configured perform catheter purchase calculations and display the catheter purchase results on the display 106. In some embodiments, the console 110 may be configured to take the target vessel depth, the insertion site location, and the angle of insertion needed to access the target vessel 152B into account when calculating the catheter purchase. In some embodiments, the console 110 may be configured to perform catheter purchase calculations for each target vessel 152A-152C detected within the target area 150 or may be configured to perform catheter purchase calculations for only the selected target vessel 152B. As illustrated in FIG. 3F, the display 106 may be configured to display one or more of the captured ultrasound images and indicate the target depth for each of the first vessel 152A, the second vessel 152B, and the third vessel 152C. The display 106 further indicates the angle of insertion 148 needed to access each of the first vessel 152A, the second vessel 152B, and the third vessel 152C. The display 106 also indicates the catheter purchase needed to access each of the first vessel 152A, the second vessel 152B, and the third vessel 152C along each indicated angle of insertion. In some embodiments, the console 110 also may be configured to generate a list of catheter options that successfully fit each of the catheter purchase criteria. Advantageously, using the ultrasound imaging system 100 to determine catheter purchase allows multiple variables (e.g., automatic determination of target vessels 152 within the target area 150, depth of target vessel 152, location of the insertion site 190 within the target area 150, the location or orientation of the needle 180 within the target area 150, the angle of insertion 148 of the needle 180, or the optimal trajectory needed to access the target vessel 152) to be used in determining catheter purchase and further allows any of the multiple variables to change while quickly determining catheter purchase.

Figure 4:
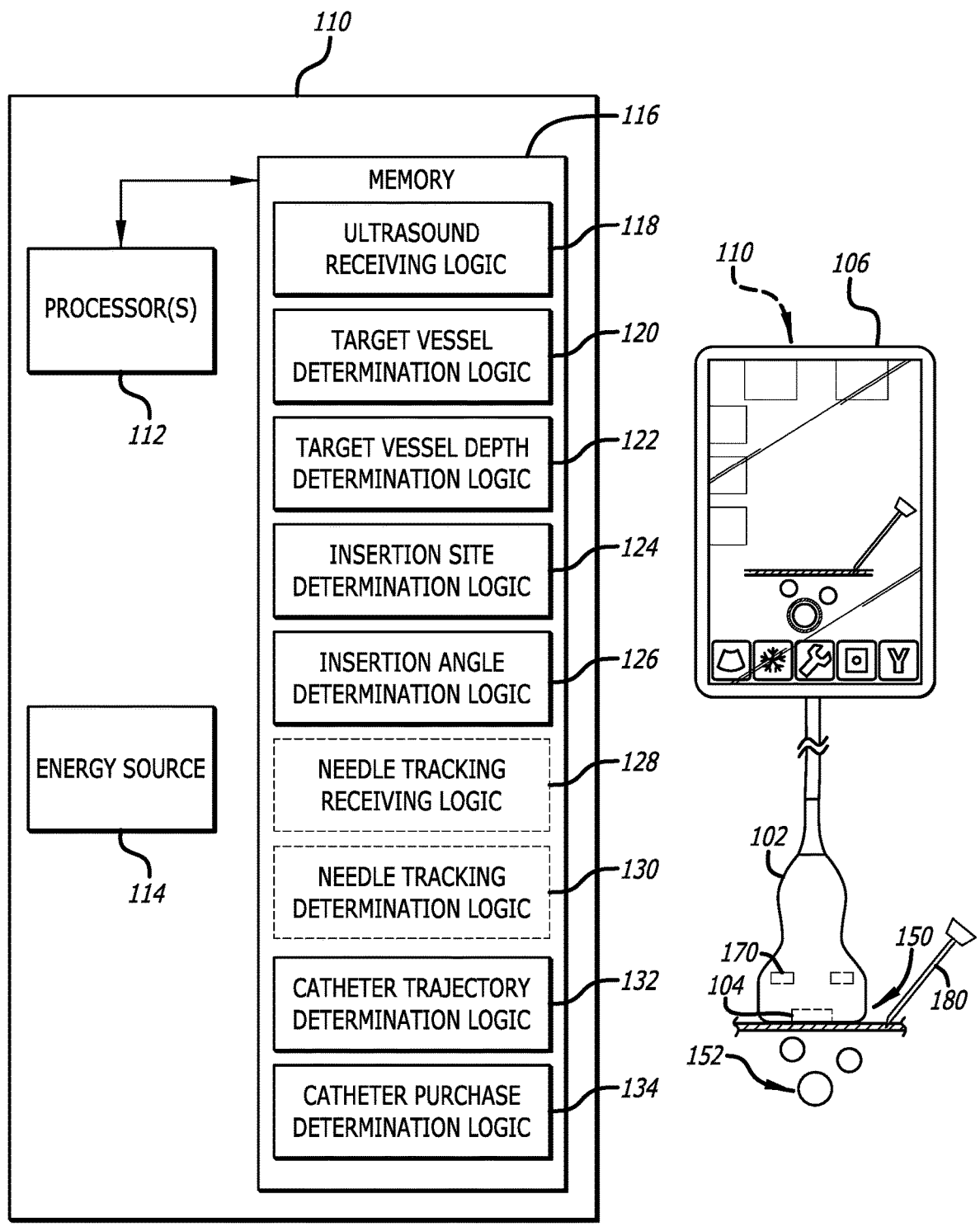
FIG. 4 illustrates a block diagram of some components of the ultrasound imaging system including a console, in accordance with some embodiments.

FIG. 4 illustrates a block diagram of a console 110 of the ultrasound imaging system 100, in accordance with some embodiments. In some embodiments, the console 110 may be in communication with each of the display 106, one or more sensors 170, and the ultrasound array 104. In some embodiments, the console 110 includes one or more processors 112, an energy source 114, non-transitory computer readable medium ("memory") 116, and a plurality of logic modules. In some embodiments, the plurality of logic modules may include one or more of the following: an ultrasound receiving logic 118, a target vessel determination logic 120, a target vessel depth determination logic 122, an insertion site determination logic 124, an insertion angle determination logic 126, a needle tracking receiving logic 128, a needle tracking determination logic 130, a catheter trajectory determination logic 132, and a catheter purchase determination logic 134. In some embodiments, the ultrasound receiving logic 118 may be configured to receive the one or more captured ultrasound images from the ultrasound array 104. In some embodiments, the target vessel determination logic 120 may be configured to determine each of the potential target vessels 152 within the target area 150. In some embodiments, the target vessel depth determination logic 122 may be configured to determine the depth from the skin surface 154 to each of the target vessels 152 within the target area 150. In some embodiments, the target vessel depth determination logic 122 may be configured to determine the depth from the insertion site 190 to each of the target vessels along the angle of insertion 148. In some embodiments, the insertion site determination logic 124 may be configured to determine the insertion site 190 within the target area 150 that may be used to access each of the target vessels 152. In some embodiments, the insertion site determination logic 124 may be configured to determine a coordinate location within the target area 150 as the insertion site 190. In some embodiments, the insertion angle determination logic 126 may be configured to determine the angle of insertion 148 necessary to access each of the target vessels 152. In some embodiments, the user may provide a desired angle of insertion 148. In some embodiments, the angle of insertion 148 may be a predetermined common angle used to access vasculature. In some embodiments, the insertion angle determination logic 126 may be configured to use the angle of the needle 180 as the needle 180 is brought in proximity to the ultrasound probe 102 to determine the angle of insertion 148. In some embodiments, the insertion angle determination logic 126 may be configured to compare the current angle of insertion 148 of the needle 180 with either the desired angle of insertion 148 as determined by the user or the current angle of insertion 148 of the needle 180 along the optimal trajectory of needle 180 necessary to access the target vessel.

In some embodiments, the needle tracking receiving logic 128 may be configured to receive data from the one or more sensors 170 configured to detect and track the magnetic signature of the needle 180. In some embodiments, the needle tracking determination logic 130 may be configured to determine the three-dimensional location and orientation of the needle 180 within the target area 150 including the angle of the needle 180 in relation to each of the target vessels 152. In some embodiments, the catheter trajectory determination logic 132 may be configured to determine the trajectory needed by the catheter 140 to access the each of the target vessels 152. In some embodiments, the catheter trajectory determination logic 132 may be configured to detect and track the trajectory of the catheter 140 within the target area 150 using the ultrasound array 104 or one or more sensors 170 when the catheter 140 includes a magnetic signature thereon. In some embodiments, the catheter purchase determination logic 134 may be configured to calculate the catheter purchase (length of catheter within tissues/vessel/and outside of body). In some embodiments, the catheter purchase determination logic 134 may be configured to calculate the catheter purchase using the angle of insertion 148, the optimal trajectory, the location of the insertion site 190, a target vessel depth, the location of the needle 180, or the like to calculate the catheter purchase.

Figure 5:
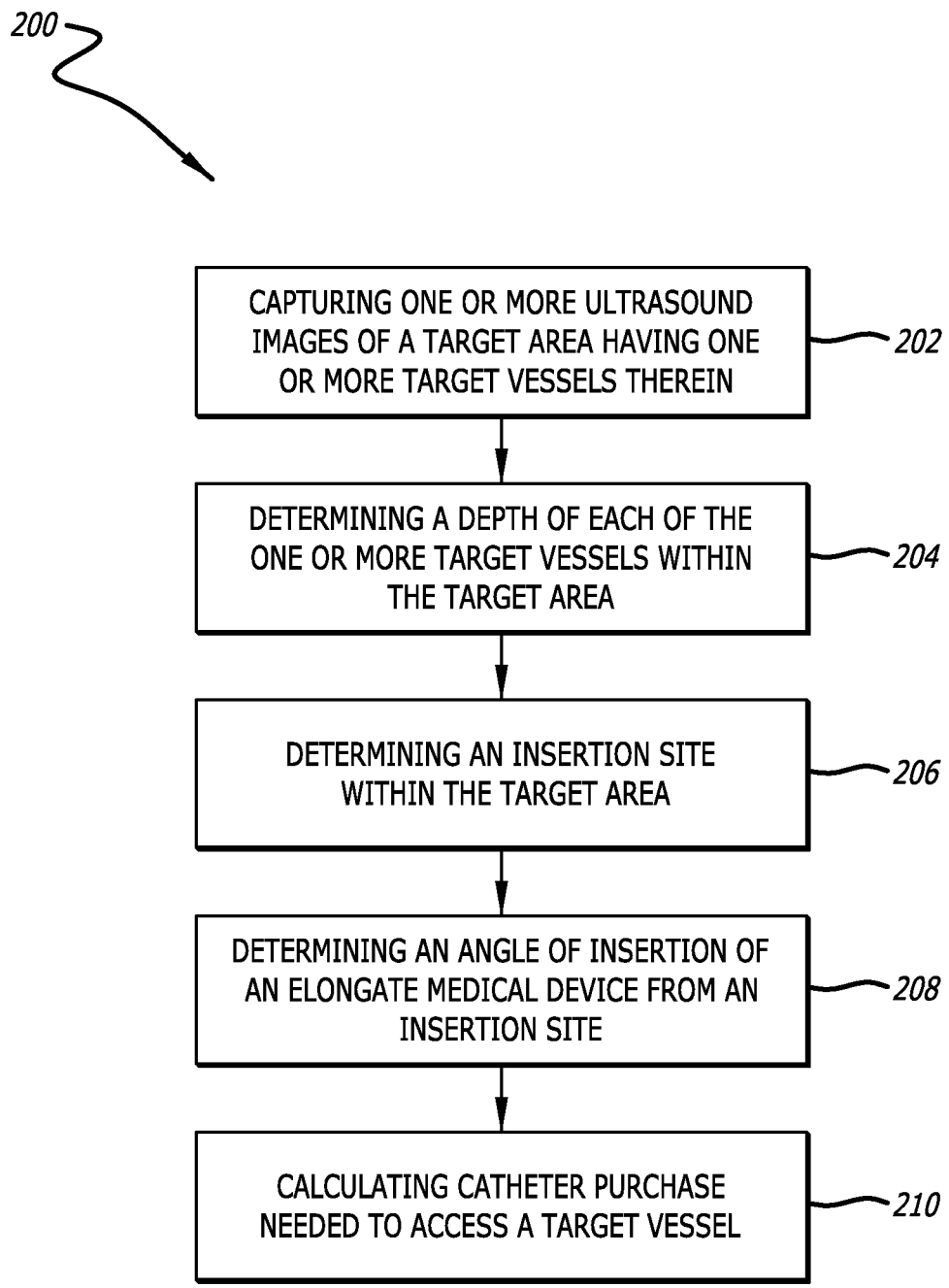
FIG. 5 illustrates a flow chart of an exemplary method of determining catheter purchase, in accordance with some embodiments.

FIG. 5 illustrates a flow chart of an exemplary method 200 determining catheter purchase, in accordance with some embodiments. In some embodiments, the method 200 includes capturing one or more ultrasound images of a target area 150 having one or more target vessels 152 (block 202). In some embodiments, capturing one or more ultrasound images of the target area 150 having one or more target vessels 152 includes using the ultrasound imaging system 100 including the ultrasound probe 102 having the ultrasound array 104 and the one or more sensors 170 coupled thereto, the ultrasound array 104 configured to capture the one or more ultrasound images of the target area 150 while the one or more sensors 170 are configured to detect and track the magnetic signature of the elongate medical device 180. Each of the ultrasound array 104 and the one or more sensors 170 in communication with the console 110.

In some embodiments, the method 200 includes determining a depth of each of one or more target vessels 152 within the target area 150 (block 204). In some embodiments, determining the depth of each of the one or more target vessels 152 within the target area 150 includes the console 110 automatically determining the depth of each of the one or more target vessels 152 from the skin surface 154 within the target area 150.

In some embodiments, the method 200 further includes determining an insertion site 190 within the target area 150 (block 206). In some embodiments, determining the insertion site 190 within the target area 150 includes the console 110 or the user determining the insertion site 190 within the target area 150. In some embodiments, determining the insertion site 190 within the target area 150 may include taking into account the depth of each of the one or more target vessels 152 in determining the insertion site 190 within the target area 150.

In some embodiments, the method 200 includes determining an angle of insertion 148 of the elongate medical device 180 from the insertion site 190 to access each of the one or more target vessels 152 (block 208). In some embodiments, determining the angle of insertion of the needle 180 from an insertion site 190 to access each of the one or more target vessels 152 includes using the one or more sensors 170 in communication with the console 110 to determine a current angle of insertion 148 of the needle 180 within the target area 150. In some embodiments, determining the angle of insertion of the needle 180 from the insertion site 190 to access each of the one or more target vessels 152 includes using the one or more sensors 170 coupled to the ultrasound probe 102, the one or more sensors configured to detect the location and orientation of the needle 180 within the target area 150, including the one or more magnetic signatures of the needle 180.

In some embodiments, determining an angle of insertion 148 from the insertion site 190 to access each of the one or more target vessels 152 includes the console 110 determining an optimal trajectory of the needle 180 from the insertion site 190 needed to access each of the one or more target vessels 152. In some embodiments, the console 110 determining an optimal trajectory of the needle 180 from the insertion site 190 needed to access each of the one or more target vessels 152 includes the console 110 determining the optimal trajectory of the needle 180 along the angle of insertion 148. In some embodiments, determining an angle of insertion 148 of the elongate medical device 180 from the insertion site 190 to access each of the one or more target vessels 152 includes the user supplying a pre-determined angle of insertion 148 to the console 110. In some embodiments, the depth of each of the one or more target vessel 152 may contribute to determining the angle of insertion 148 of the needle 180 from the insertion site 190 to access each of the one or more target vessels 152.

In some embodiments, the method 200 includes calculating catheter purchase needed to access each of the target vessels 152 (block 210). In some embodiments, calculating catheter purchase needed to access each of the target vessels 152 includes the console 110 using one or more of: the depth of the target vessel 152, the angle of insertion 148 of the needle 180, the location of the insertion site 190, or the optimal trajectory of the needle 180 needed to access the target vessel 152 to calculate catheter purchase. In some embodiments, calculating catheter purchase needed to access each of the target vessels 152 includes calculating the total length of the catheter 140 needed to access each of the target vessels 152 from the insertion site 190. In some embodiments, the total length of the catheter 140 includes the first length 142 outside of the tissues 160, the second length 144 within the tissues 160, and the third length 146 within the target vessel 152. In some embodiments, calculating catheter purchase needed to access each of the target vessels 152 includes identifying one or more catheters 140 having the catheter purchase length necessary to access the one or more target vessels 152. In some embodiments, identifying one or more catheters 140 having the catheter purchase length necessary to access the one or more target vessels 152 includes the display 106 in communication with the console 110 identifying the one or more catheters 140 having the catheter purchase length necessary to access the one or more target vessels 152. In some embodiments, calculating catheter purchase includes calculating catheter purchase as the needle 180 is actively moved through the target area 150, including changing the angle of insertion 148.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system used to place a catheter within a first vessel of a plurality of vessels, comprising:

an ultrasound probe having an ultrasound array configured to capture one or more ultrasound images of the plurality of vessels within a target area;

a medical device tracking system including a sensor configured to sense a magnetic signature of a needle within the target area, wherein the medical device tracking system is disposed on the ultrasound probe;

a display; and a console in communication with the ultrasound probe, the display, and the medical device tracking system, the console including a processor and non-transitory, computer-readable medium having logic stored thereon, wherein the logic, when executed by the processor, causes performance of operations including:

detecting a depth of each of the plurality of vessels within the one or more ultrasound images, determining an angle of insertion of the needle based on a position or an orientation of the needle, wherein the position or the orientation is based on the magnetic signature of the needle sensed by the medical device tracking system, determining a catheter purchase and a corresponding insertion angle for the needle to access each of the plurality of vessels based on the depth of each of the plurality of vessels, wherein the catheter purchase includes a length of a catheter for accessing one of the plurality of vessels, and displaying, on the display, the one or more captured ultrasound images, and for each of the plurality of vessels: the depth of the vessel, the angle of insertion of the needle from an insertion site to access a target vessel, and the catheter purchase of the vessel that corresponds to access of the vessel as the angle of insertion.

2. The ultrasound imaging system according to claim 1, wherein the depth of each of the plurality of vessels is determined relative to a skin surface in the target area.

3. The ultrasound imaging system according to claim 1, wherein determining the catheter purchase is further based on the insertion site of the needle.

4. The ultrasound imaging system according to claim 1, wherein the insertion site is a coordinate location within the target area.

5. The ultrasound imaging system according to claim 1, wherein the medical device tracking system includes a plurality of sensors configured to sense the magnetic signature of the needle within the target area.

6. The ultrasound imaging system according to claim 1, wherein the logic, when executed by the processor, causes performance of further operations including:

displaying one or more icons relating to the catheter purchase on the display.

7. A method of determining a catheter purchase, comprising:

capturing one or more ultrasound images of a target area, the one or more ultrasound images having a plurality of vessels therein;

determining a depth of each of the plurality of vessels;

determining an angle of insertion of a needle based on a position or an orientation of the needle based on a magnetic signature of the needle;

determining the catheter purchase and a corresponding insertion angle for the needle to access each of the plurality of vessels based on the depth of each of the plurality of vessels, wherein the catheter purchase includes a length of a catheter for accessing one of the plurality of vessels; and displaying, on the display, the one or more captured ultrasound images, and for each of the plurality of vessels: the depth of the vessel, the angle of insertion of the needle from an insertion site to access the target area, and the catheter purchase of the vessel that corresponds to access of the vessel as the angle of insertion.

8. The method according to claim 7, wherein the one or more ultrasound images of the target area is obtained from an ultrasound probe having an ultrasound array in communication with a console.

9. The method according to claim 7, wherein determining the depth of each of the plurality of vessels is determined relative to a skin surface within the target area.

10. The method according to claim 7, wherein determining the catheter purchase is further based on the insertion site within the target area.

11. The method according to claim 7, wherein the insertion site is a coordinate location within the target area.

12. The method according to claim 7, wherein the magnetic signature of the needle is sensed by a medical device tracking system that includes a plurality of sensors, and wherein the magnetic signature of the needle is obtained by the plurality of sensors.

13. The method according to claim 7, wherein determining the catheter purchase is further based on the angle of insertion of the needle.

14. The method according to claim 7, further comprising:

displaying one or more icons relating to the catheter purchase of the plurality of vessels on a display of a console device.

15. The method according to claim 7, wherein determining the catheter purchase includes identifying one or more catheters having a catheter purchase length necessary to access a first vessel of the plurality of vessels.

16. The method according to claim 7, wherein determining the catheter purchase includes a set of catheters configured to access the plurality of vessels.

17. The method according to claim 7, further comprising:

repeatedly determining the catheter purchase for each of the plurality of vessels as the needle is moved through the target area.

* * * * *